US00PP30879P2

(12) United States Plant Patent
Finn

(10) Patent No.: US PP30,879 P2
(45) Date of Patent: Sep. 10, 2019

(54) BLACKBERRY PLANT NAMED 'TWILIGHT'

(50) Latin Name: ***Rubus* subg. *Rubus* Watson**
Varietal Denomination: Twilight

(71) Applicant: The United States of America, as Represented by the Secretary of Agriculture, Washington, DC (US)

(72) Inventor: Chad E. Finn, Corvallis, OR (US)

(73) Assignee: The United States of America, as Represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 15/998,301

(22) Filed: Aug. 2, 2018

(51) Int. Cl.
*A01H 5/08* (2018.01)
*A01H 6/74* (2018.01)

(52) U.S. Cl.
USPC ..... Plt./203

(58) Field of Classification Search
USPC ..... Plt./156, 203
See application file for complete search history.

*Primary Examiner* — Susan McCormick Ewoldt
*Assistant Examiner* — Karen M Redden
(74) *Attorney, Agent, or Firm* — John Fado; Ariel Atkinson

(57) ABSTRACT

A new and distinct blackberry cultivar that originated from seed produced from a cross between the thornless female blackberry plant 'Ouachita' (U.S. Plant Pat. No. 17,762) and the thornless, male parent blackberry plant 'ORUS 2867-4' (unpatented)). This new blackberry cultivar can be distinguished by being fairly early ripening for a semi-erect blackberry, by its large sized, very firm berries with tough skin and a crisp texture when eaten and excellent flavor, by its high yields borne on a vigorous plant with a semi-erect type growth habit and by its completely thornless canes.

4 Drawing Sheets

Latin name of the genus and species of the plant claimed: 'Twilight' is a blackberry plant that is *Rubus* subg. *Rubus* Watson.

Variety denomination: The new blackberry plant claimed is of the variety denominated 'Twilight' *Rubus* subg. *Rubus* Watson.

BACKGROUND OF THE NEW PLANT

The present invention relates to a new and distinct blackberry cultivar designated 'Twilight' and botanically known as *Rubus* subg. *Rubus* Watson. This new blackberry cultivar was discovered in Corvallis, Oreg. in August 2012 and originated from a cross between the thornless female blackberry plant 'Ouachita' (U.S. Plant Pat. No. 17,762) and the thornless, male parent blackberry plant 'ORUS 2867-4' (unpatented). 'ORUS 2867-4' (unpatented) was a selection from a cross of the thornless semi-erect blackberry 'Triple Crown' (unpatented) and a thorny trailing blackberry selection 'ORUS 1393-1' (unpatented). 'Twilight's spinelessness was originally derived from 'Merton Thornless' (U.S. Plant Pat. No. 571). The original seedling of the new cultivar was asexually propagated at a nursery in Benton County, Oreg. The new cultivar was established in vitro from a cane cutting and microcuttings have been taken and rooted from this sort of culture. The present invention has been found to be stable and reproduce true to type through successive asexual propagations.

SUMMARY OF THE NEW PLANT

The following are the most outstanding and distinguishing characteristics of this new cultivar when grown under normal horticultural practices in Oregon. First, the new cultivar has a high plant vigor as compared to semi-erect blackberry 'Loch Ness' (U.S. Plant Pat. No. 6,782); second, the new cultivar has a semi-erect growth habit with thornless canes; third, the new cultivar has an early date for 50% of ripe fruit compared to 'Chester Thornless' (unpatented) and 'Triple Crown' (unpatented) but not as early as 'Eclipse' (U.S. patent application Ser. No. 15/731,503) or 'Galaxy' (U.S. Plant Pat. No. 30,062); fourth, the new cultivar has a very firm fruit with abrasion-resistant, tough skin compared to 'Triple Crown (unpatented) and 'Chester Thornless' (unpatented); fifth, the new cultivar has excellent flavor compared to 'Chester Thornless' (unpatented) and 'Loch Ness' (U.S. Plant Pat. No. 6,782); and sixth, the new cultivar has larger fruit than those of 'Chester Thornless' (unpatented) and similar to those of 'Triple Crown' (unpatented).

BRIEF DESCRIPTION OF THE PHOTOGRAPHS

This new blackberry plant is illustrated by the accompanying photographs that show the flowers, fruit and entire plants; the colors shown are as true as can be reasonably obtained by conventional photographic procedures.

Figure 1:
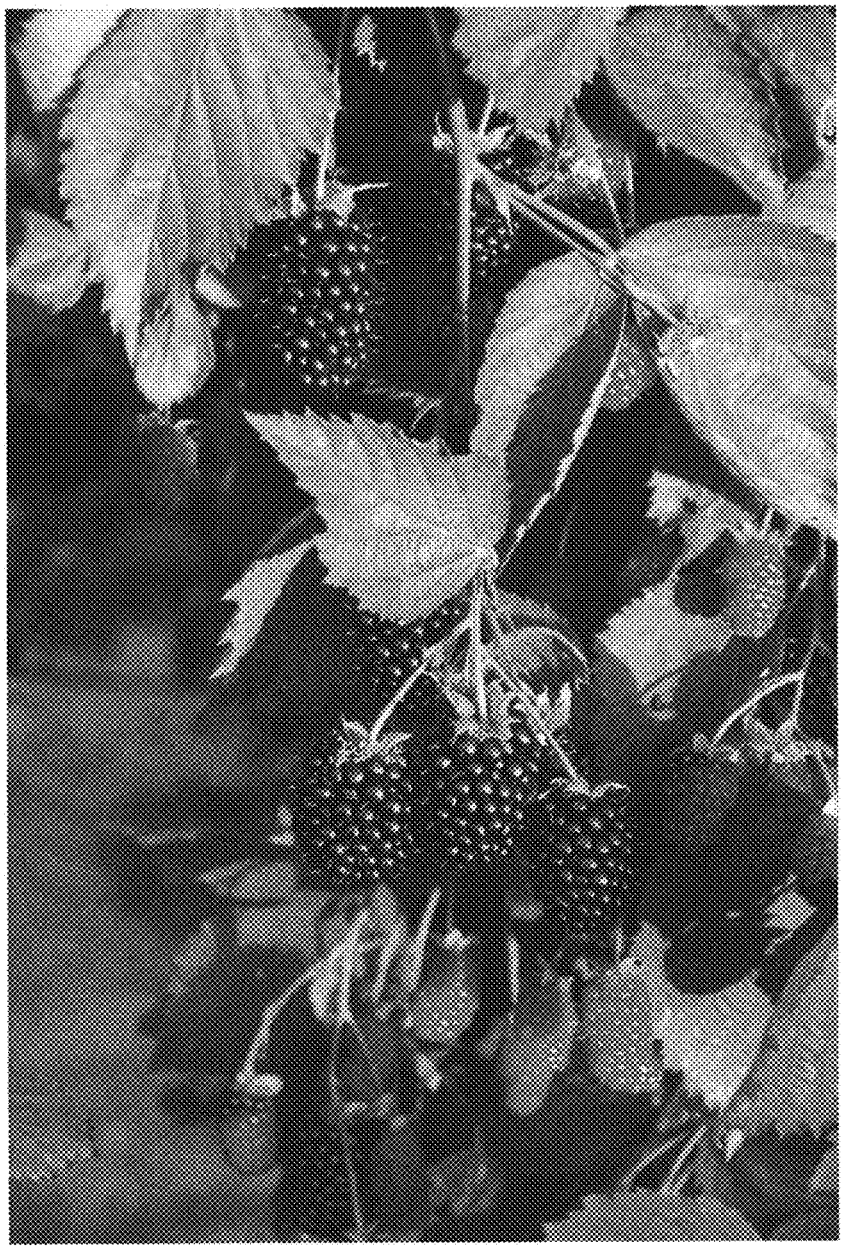
FIG. 1 shows typical fruiting cluster with ripe fruit 'Twilight'.
Figure 2:
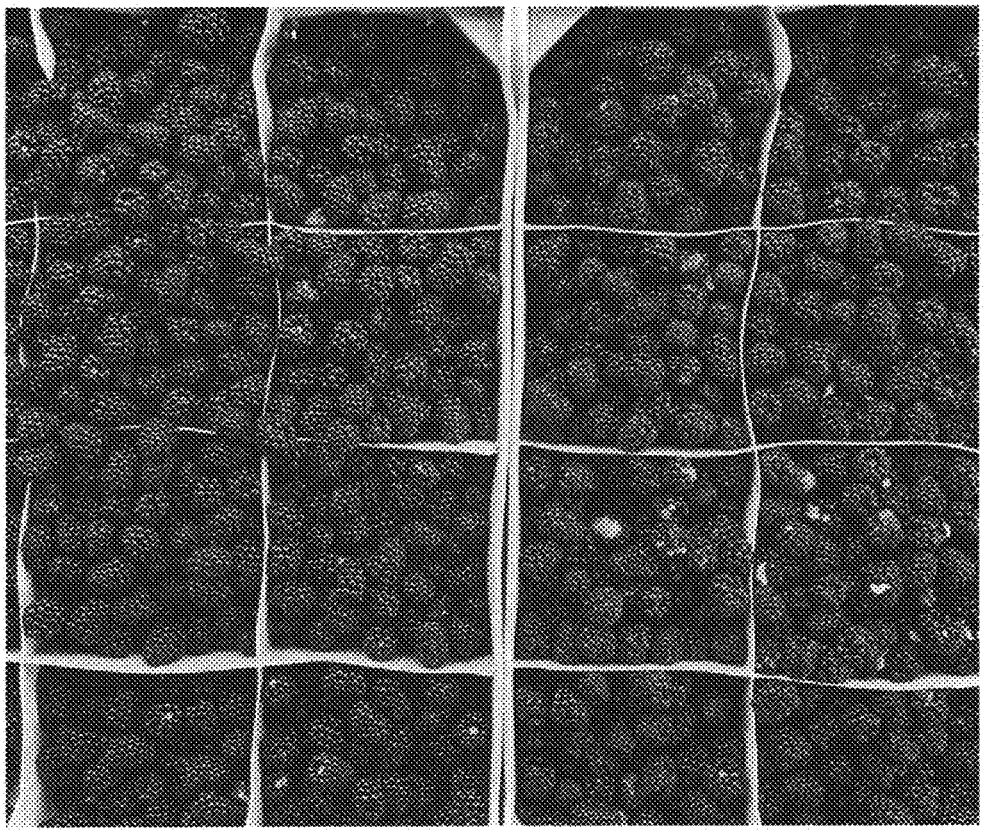
FIG. 2 shows a flat of harvested 'Twilight' fruit (left) compared to a flat of 'Chester Thornless' (unpatented) fruit (right).
Figure 3:
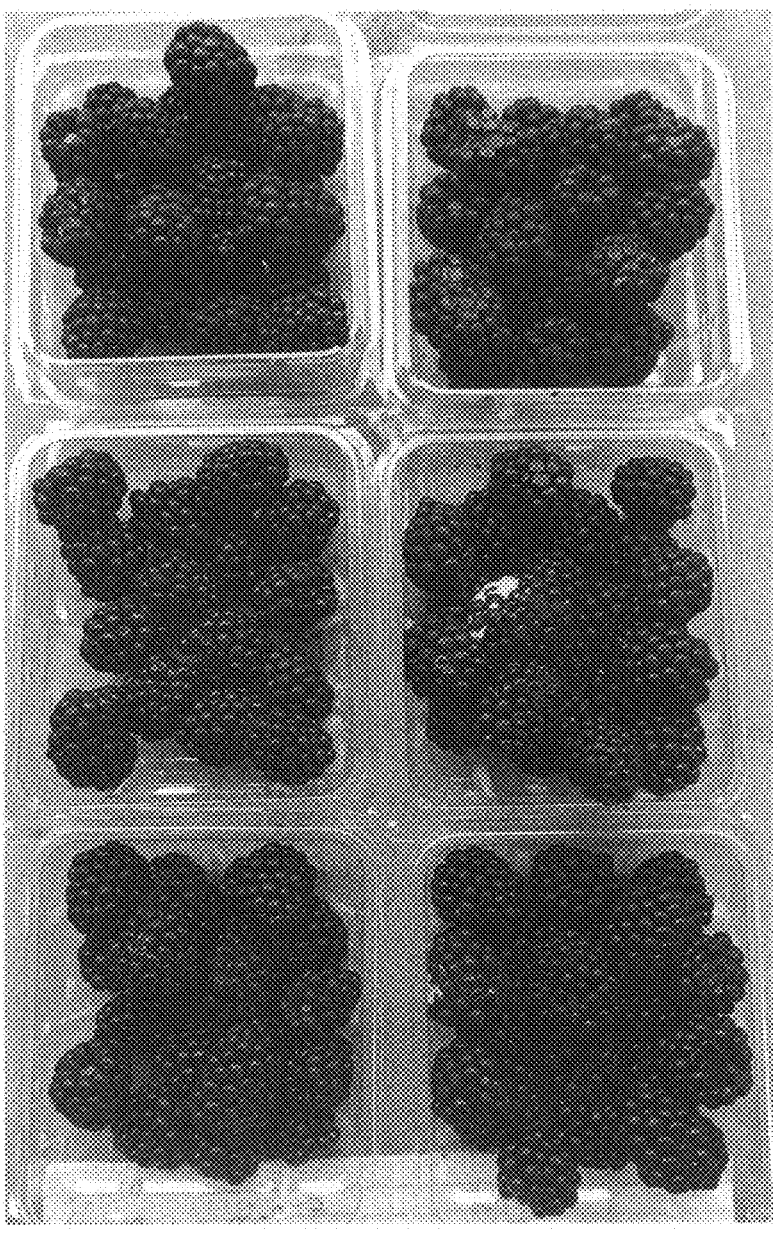
FIG. 3 shows three clamshells of 'Twilight' fruit (left column) compared to 'Chester Thornless' (unpatented) fruit (right column) after 21 days of refrigerated storage at ~1° C.
Figure 4:
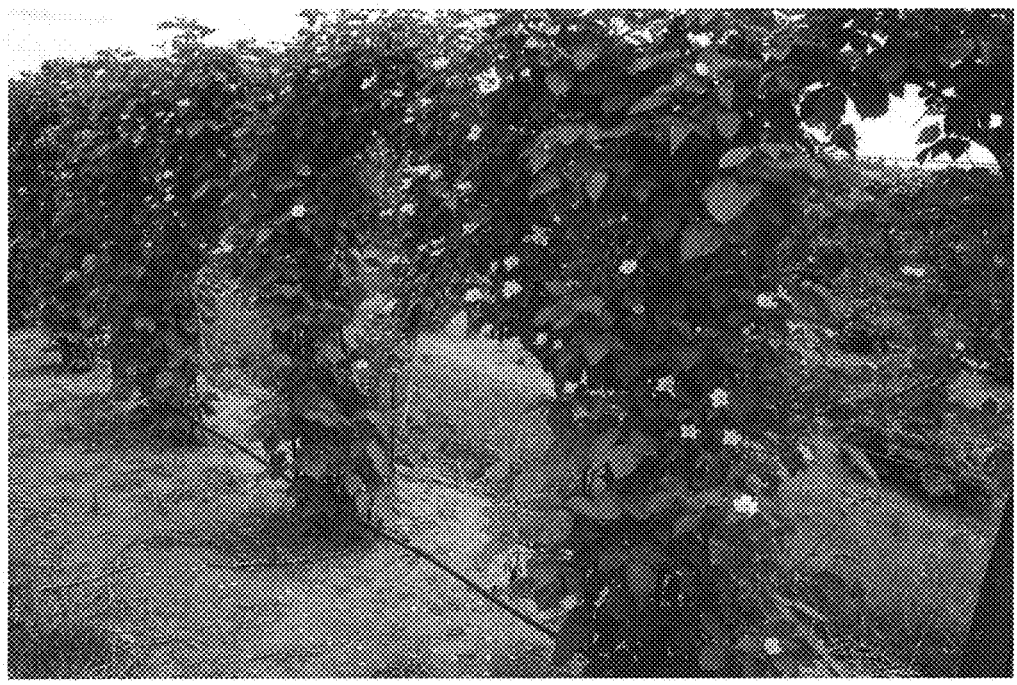

FIG. 4 shows entire flowering 3-year old 'Twilight' plants. As is typical for commercial production, semi-erect blackberry primocanes are topped at ~1 m and the primocanes and laterals that develop after topping are tied to a two wire trellis with the lower wire approximately 1.0 m above the ground and the upper wire approximately 1.5 m above the ground.

DETAILED DESCRIPTION OF THE NEW CULTIVAR

The following description of 'Twilight' is based on observations taken from 2012 to 2017 growing seasons in trials in Corvallis and Aurora, Oreg. This description is in accordance with UPOV terminology. Color designations, color descriptions and other phenotypical descriptions may deviate from the stated values and descriptions depending upon variation in environmental, seasonal, climatic and cultural conditions. 'Twilight' has not been observed under all possible environmental conditions. Color terminology follows The Royal Horticultural Society Colour Chart. London (R.H.S.) ($5^{th}$ edition, 2007).

Table 1 shows important plant characteristics of the new cultivar. Characteristics include plant vigor, growth habit, date 50% of fruit were ripe, weight of primary fruit, firmness of fruit flavor of fruit and winter tolerance in Aurora, Oreg. (45° 16' 49" N/122° 44' 50" W) and Lynden, Wash. (48° 56' 48" N/122° 27' 2" W).

TABLE 1

| Characteristic | 'Twilight' |
|---|---|
| Plant vigor | High vigor, similar to 'Eclipse', less vigorous than 'Chester Thornless' and 'Triple Crown' and more vigorous than 'Loch Ness' |
| Growth habit | Semi-erect |
| Date 50% of fruit were ripe | 21 July, early compared to 'Triple Crown' and 'Chester Thornless'; Later than 'Eclipse' |
| Weight of primary fruit (g) | 8.7 g, larger than 'Chester Thornless', similar in size to 'Triple Crown' |
| Firmness of fruit | Excellent, much firmer than 'Triple Crown' and firmer than 'Chester Thornless' |
| Skin toughness of fruit | Excellent, much better than 'Triple Crown' and better than 'Chester Thornless' |
| Flavor of fruit | Very good, excellent compared to 'Chester Thornless', similar to 'Triple Crown' and 'Eclipse' |
| Winter tolerance in Aurora, Oregon (45 16' 49" N/122 44' 50" W) | Excellent, comparable to 'Triple Crown', 'Chester Thornless', and 'Navaho' (U.S. Plant Pat. No. 6,679) |
| Winter tolerance in Lynden, Washington (48 56' 48" N/122 27' 2" W) | Excellent. comparable to 'Triple Crown' and 'Chester Thornless' |

Table 2 shows floricane and mature primocane characteristics of the new cultivar. Characteristics include diameter at base, diameter at midpoint, diameter at terminus, internode length at base, internode length at midpoint, internode length at terminus, presence of spines further than 0.6 m from the soil surface, presence of spines less than 0.6 m from the soil surface, floricane color at base, floricane color at midpoint, floricane lateral length, floricane lateral strength, primocane color at base, primocane color at midpoint, and primocane color at terminus. The characteristics of floricane color at terminus, floricane length, and floricane length (range) are not available for the new cultivar as the standard practice for the cultivar is to remove the tips of primocanes (which become floricanes after receiving winter chilling) to encourage fruiting.

TABLE 2

| Characteristic | 'Twilight' |
|---|---|
| Diameter at base (cm) | 2.00 |
| Diameter at midpoint (cm) | 1.23 |
| Diameter at terminus (cm) | 0.37 |
| Internode length at base (cm) | 11.93 |
| Internode length at midpoint (cm) | 2.87 |
| Internode length at terminus (cm) | 2.87 |
| Presence of spines further than 0.6 m from the soil surface | Absent |
| Presence of spines less than 0.6 m from the soil surface | Absent |
| Floricane color at base | 146A |
| Floricane color at midpoint | 144A w/175A tint |
| Floricane lateral length | Medium |
| Floricane lateral strength | Medium |
| Primocane color at base | 144A |
| Primocane color at midpoint | 144A w/176A streaks |
| Primocane color at terminus | 144A w/185A tint |

Table 3 shows floricane foliage characteristics of the new cultivar. Floricane characteristics include mature compound leaf width, mature compound leaf length, number of leaflets per floricane compound leaf, mature leaflet shape, mature leaflet apex, mature leaflet base, mature terminal leaflet width, mature terminal leaflet length, mature first lateral leaflet width, mature first lateral leaflet length, leaflet margin, leaflet serration teeth length, leaflet serration teeth width at base, pubescence on floricane leaflet: upper surface, pubescence on floricane leaflet: undersurface, floricane leaf color abaxial, floricane leaf color adaxial, petiole length, petiolule length: terminal leaflet, petiolule length: first distal leaflet, petiolule color: abaxial, petiolule color: adaxial, stipule length, and stipule width.

TABLE 3

| Characteristic | 'Twilight' |
|---|---|
| Mature compound leaf width (cm) | 16.65 |
| Mature compound leaf length (cm) | 13.44 |
| Number of leaflets per floricane compound leaf | 3.00 |
| Mature leaflet shape | Ovate |
| Mature leaflet apex | Acute |
| Mature leaflet base | Roundly truncate |
| Mature terminal leaflet width (cm) | 7.25 |
| Mature terminal leaflet length (cm) | 9.25 |
| Mature first lateral leaflet width (cm) | 6.43 |
| Mature first lateral leaflet length (cm) | 8.52 |
| Leaflet margin | Serrated |
| Leaflet serration teeth length | 0.33 |
| Leaflet serration teeth width at base | 0.38 |
| Pubescence on floricane leaflet: upper surface | Light pubescence |
| Pubescence on floricane leaflet undersurface | Heavy, dense pubescence |
| Floricane leaf color abaxial | 137A |
| Floricane leaf color adaxial | 138B |
| Petiole length (cm) | 5.72 |
| Petiole color adaxial | 165A |
| Petiole color abaxial | N144D |
| Petiolule length terminal leaflet (cm) | 1.52 |
| Petiolule length first distal leaflet (cm) | 2.11 |
| Petiolule color abaxial | 165A |
| Petiolule color adaxial | N144D |
| Stipule length (cm) | 1.00 |
| Stipule width (cm) | 0.24 |
| Stipule attitude | Erect |

Table 4 shows flower and flowering characteristics of the new cultivar. Flower and flowering characteristics include date 1st bloom, date full bloom, date last bloom, petal color, the number flowers per cluster, the number of petals per flower, flower diameter, petal length, petal width, the number of sepals per flower, peduncle length, rachis length, peduncle color, and cyme type.

TABLE 4

| Characteristic | 'Twilight' |
|---|---|
| Date 1st bloom | May 13 |
| Date full bloom | May 20 |
| Date last bloom | May 30 |
| Petal color adaxial and abaxial surfaces | 69C |
| Number flowers per cluster | 8.83 |
| Number of petals per flower | 5.33 |
| Flower diameter (cm) | 32.45 |
| Petal length (cm) | 14.28 |
| Petal width (cm) | 11.33 |
| Petal texture adaxial and abaxial | No pubescence |
| Number of sepals per flower | 4.83 |
| Peduncle length (cm) | 3.67 |
| Rachis length (cm) | 10.85 |
| Peduncle color | N144A streaked w/185A |
| Cyme type | Elongate simple cyme |

Table 5 shows fruit and fruiting characteristics of the new cultivar. Fruit and fruiting characteristics include date 5% of fruit were ripe, date 50% of fruit were ripe, date 95% of fruit were ripe, weight of primary fruit, weight of secondary fruit, diameter of primary fruit at equator, diameter of 2° fruit at equator, diameter of 1° fruit at poles: tip, diameter of 1° fruit at poles: base, diameter of 2° fruit at poles: tip, diameter of 2° fruit at poles: base, berry length 1° fruit, berry length 2° fruit, ratio of primary fruit length to width, shape description, uniformity of berry shape, color when full ripe, number of drupelets per fruit, individual seed weight, glossiness, firmness, flavor, texture of fruit when chewed, drupelet skin resistance to abrasion, ease of separation of fruit from pedicel, machine harvestability, resistance to heat damage of fruit, berries per inflorescence—mean, berries per inflorescence range, soluble solids (%; in Brix), pH, titratable acidity (% as citric acid), yield (actual $kg \cdot plt^{-1}$), disease response, and red berry mite response.

TABLE 5

| Characteristic | 'Twilight' |
|---|---|
| Date 5% of fruit were ripe | Jul. 10 |
| Date 50% of fruit were ripe | Jul. 21 |
| Date 95% of fruit were ripe | Aug. 9 |
| Weight of primary fruit (g) | 8.03 |
| Weight of secondary fruit (g) | 5.91 |
| Weight of tertiary fruit (g) | 6.00 |
| Diameter of primary fruit a t equator (cm) | 2.16 |
| Diameter of 2 fruit at equator (cm) | 2.22 |
| Diameter of 3 fruit at equator (cm) | 2.03 |
| Diameter of 1 fruit at poles: tip (cm) | 1.70 |
| Diameter of 1 fruit at poles: base (cm) | 2.18 |
| Diameter of 2 fruit at poles: tip (cm) | 1.70 |
| Diameter of 2 fruit at poles: base (cm) | 2.08 |
| Diameter of 3 fruit at poles: tip (cm) | 1.61 |
| Diameter of 3 fruit at poles: base (cm) | 1.96 |
| Berry length primary fruit (cm) | 2.85 |
| Berry length 2 fruit (cm) | 2.51 |
| Berry length 3 fruit (cm) | 2.47 |
| Ratio of primary fruit length to width | 1.32 |
| Shape description | Blocky |
| Uniformity of berry shape | Consistent shape |
| Color | when full ripe 203A |
| Number of drupelets per fruit | 68.50 |
| Total seed weight per fruit (mg) | 199.30 |
| Individual seed weight (mg) | 2.96 |
| Glossiness | Very glossy |

TABLE 5-continued

| Characteristic | 'Twilight' |
|---|---|
| Firmness | Very firm |
| Flavor | Very good flavor |
| Texture of fruit when chewed | Good |
| Drupelet skin resistance to abrasion | Excellent |
| Ease of separation of fruit from pedicel | Medium |
| Machine harvestability | Good |
| Resistance to heat damage of fruit | Good |
| Berries per inflorescence - mean | 7.50 |
| Berries per inflorescence range | 7-8 |
| Soluble solids (%; in Brix) | 13.07 |
| pH | 3.51 |
| Titratable acidity (% as citric acid) | 8.58 |
| Yield (actual kg · plt-1) | 9.78 |
| Disease response | Under a typical, minimal, disease management program does not exhibit any particular disease problems |
| Red berry mite response | Moderate susceptibility |

COMPARISON WITH PARENTAL AND COMMERCIAL CULTIVARS

'Twilight' differs from the female parent blackberry plant 'Ouachita' (U.S. Plant Pat. No. 17,762) in that it has a semi-erect type plant growth habit, is more productive, with larger (8.7 g) and sweeter (13% Brix) fruit that have a pleasant crispness when eaten, while 'Ouachita' (U.S. Plant Pat. No. 17,762) has an erect type plant growth habit, is less productive, has smaller (7.0 g) and less sweet (11% Brix) fruit that, while firm, are not crisp when eaten.

'Twilight' differs from the male parent blackberry plant 'ORUS 2867-4' (unpatented) in that it is 7 days earlier ripening with large sized (8.7 g) fruit that are firm with a tough skin and have a lower incidence of fruit defects due to excessive heat and UV light damage, while 'ORUS 2867-4' (unpatented) is 7 days later ripening with medium-large (7.2 g) fruit that are soft with tender skin and are prone to heat and UV light damage.

'Twilight' is 7-14 days earlier ripening than other commercial semi-erect fresh market blackberries such as 'Triple Crown' (unpatented) or 'Chester Thornless' (unpatented). 'Twilight' ripens 4-5 d later than the semi-erect blackberry 'Loch Ness' (U.S. Plant Pat. No. 6,782), 'Eclipse' (U.S. patent application Ser. No. 15/731,503), 'Galaxy' (U.S. Plant Pat. No. 30,062), and 'Von' (U.S. Plant Pat. No. 27,299). 'Twilight' is a fresh market blackberry and has had excellent fruit quality after 7 days in refrigerated storage in plastic clam shell packaging at 1° C. compared to fruit from 'Eclipse' (U.S. patent application Ser. No. 15/731,503), 'Triple Crown' (unpatented), and 'Von' (U.S. Plant Pat. No. 27,299). 'Twilight' has a pleasantly crisp, firm texture when eaten, firmer than 'Triple Crown' (unpatented), and with fewer noticeable seeds than 'Chester Thornless' (unpatented). 'Twilight' was as high yielding as 'Chester Thornless' (unpatented) and 'Triple Crown' (unpatented), and higher yielding than 'Eclipse' (U.S. patent application Ser. No. 15/731,503). 'Twilight' fruit are sweeter than those of 'Chester Thornless' (unpatented) but not as sweet as those of 'Triple Crown' (unpatented) and comparable to 'Eclipse' (U.S. patent application Ser. No. 15/731,503).

I claim:

1. A new and distinct cultivar of thornless blackberry plant, substantially as illustrated and described, characterized by its large sized fruit that are sweet, crisp, firm, and have a very tough skin.

* * * * *